United States Patent [19]

Engelhardt et al.

[11] Patent Number: 4,601,306

[45] Date of Patent: Jul. 22, 1986

[54] APPARATUS FOR ASCERTAINING AND/OR KEEPING CONSTANT THE MIXING RATIO OF A LIQUID MIXTURE

[75] Inventors: Ernst Engelhardt, Augsburg; Georg Kölbl, Neusäss, both of Fed. Rep. of Germany

[73] Assignee: Balwin - Gegenheimer GmbH, Fed. Rep. of Germany

[21] Appl. No.: 709,958

[22] Filed: Mar. 8, 1985

[30] Foreign Application Priority Data

Mar. 27, 1984 [DE] Fed. Rep. of Germany ....... 3411163

[51] Int. Cl.$^4$ ............................................ G05D 11/13
[52] U.S. Cl. ......................................... 137/91; 73/452; 73/453
[58] Field of Search ................................ 73/451–453; 137/91

[56] References Cited

U.S. PATENT DOCUMENTS

| | | | |
|---|---|---|---|
| 2,543,522 | 2/1951 | Cohen | 137/91 |
| 3,994,175 | 11/1976 | Yamaguchi | 73/453 |
| 4,398,554 | 8/1983 | Kondo | 137/91 |
| 4,474,204 | 10/1984 | West | 137/91 X |

FOREIGN PATENT DOCUMENTS 39059 3/1980 Japan ..................... 73/453

*Primary Examiner*—Robert G. Nilson
*Attorney, Agent, or Firm*—Jones, Tullar & Cooper

[57] ABSTRACT

In the case of an apparatus for ascertaining and keeping constant the concentration of alcohol in the plate dampening fluid used in an offset litho press, having a float vessel with an inlet and an overflow such that the float controls the supply of alcohol in accordance with its level relative to the fluid, a high degree of accuracy and a simple possibility of displaying and storing the concentration data is made possible by having a marker mounted on the float and having a vertical scale of zones marked thereon which may be sensed without mechanical contact by a sensing device at a fixed height. Furthermore the sensing device has a control signal output connected with a controller which is furthermore acted upon by a set point signal and has at least one output signal connection for controlling a valve regulating the supply of alcohol to said fluid.

11 Claims, 3 Drawing Figures

U.S. Patent    Jul. 22, 1986    4,601,306
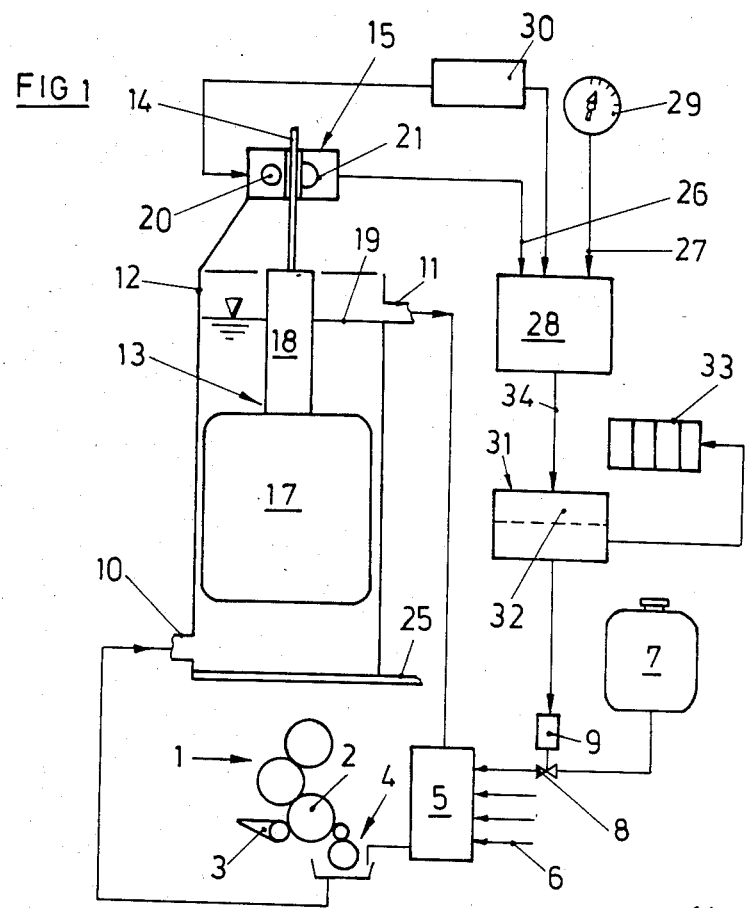
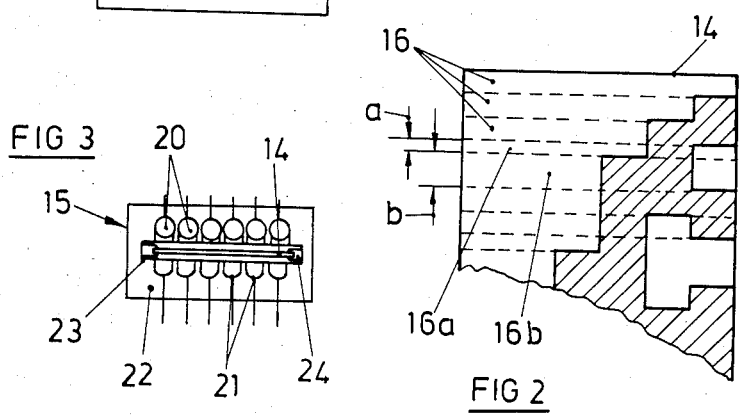

APPARATUS FOR ASCERTAINING AND/OR KEEPING CONSTANT THE MIXING RATIO OF A LIQUID MIXTURE

BACKGROUND OF THE INVENTION

The present invention relates to an apparatus for ascertaining and/or keeping constant the mixing ratio of a liquid mixture, and more specifically but not exclusively for measuring and keeping constant the alcohol concentration of the dampening fluid used in offset lithography, comprising a float located in a vessel having a fluid supply inlet and an overflow connecting it with a fluid circuit, said float cooperating with a device worked in a way dependent on the level of the float in the fluid.

In the case of one known device of this sort for keeping constant the concentration of alcohol used in dampening liquid in an offset litho press, a valve is operated mechanically by the float, such valve then controlling a line for the supply of alcohol to be mixed with the fluid. Because of the high forces needed to open and close the valve in this case, which have to be provided by the float, it is not possible to keep the concentration constant within anything but very wide limits. A further drawback with this known device is that there is no possibility of indicating and recording or storing of the instantaneous alcohol concentration. Although proximity switches have been used as a remedy in conjunction with the float in order to control the valve for the pipe supplying the alcohol to be mixed with the dampening fluid, and in this case it was no longer necessary for the float to provide the forces needed for opening and shutting the valve, it was still not possible for the instantaneous alcohol concentration values to be indicated and stored. Furthermore, since the proximity sensors have to be mechanically secured in place the set point of the system may not be adjusted and remains at a certain value, unless a complex operation is performed to adjust the position of the proximity sensors.

SHORT SUMMARY OF THE INVENTION

Taking these prior art systems as a starting point, one object of the present invention is therefore to avoid the shortcomings of such known devices.

A further object of the invention is to design an apparatus of the sort denoted that not only ensures a high degree of accuracy but furthermore offers a simple way of indicating and/or storing the values detected.

These and further objects are effected in keeping with the invention inasfar as there is a marker able to be operated by the float and which has superposed or vertically aligned indicating zones, there being a sensing device adapted to sense the position of the marker and being at a fixed height, the output signal being fed to the control signal input connection of a controller, which in addition to such connection has a set point input connection and at least one control output.

Such an automatic controller makes it possible for readings to be taken contactlessly so that a high standard of accuracy is vouched for. It is readily possible for example to keep the alcohol concentration constant within a tolerance range of as small as 0.5% in the dampening fluid, while on the other hand a modification of the desired concentration is easily performed. To this end it is only necessary to change the set point of the controller. A further beneficial effect of the device is that the marker with its indicating zones practically makes possible a digitalisation of the readings or values so that such values may be stored and displayed. Such storing of the values then makes possible averaging of all the values read within a given period of time so that peaks are smoothed out, something that also has an advantageous effect on the obtainable accuracy. It will be seen from this that the invention attains its aim using simple and low-price means.

The level of the float in the fluid is a function of the specific gravity of the fluid supplied into the vessel. The specific gravity of the fluid depends on the concentration of the individual components, viz. in the case of a dampening fluid, the alcohol concentration for example. This dependency is generally not linear. Therefore it is best to design the marker so that the indicating zones placed one over the other are each associated with a given concentration of the fluid and denote equally large ranges in concentration. The heights of the indicating zones in each case correspond to the change in the concentration between the limits of the respective associated zone. This practically leads to a linearisation of the above-quoted relation between the specific gravity and the concentration.

In accordance with a further useful outgrowth of the invention, it is possible for the float to have a submersible member that is connected with the marker by way of a rod fixed thereto having a constant diameter along its full length that is equal to at least the full height of the set of vertically aligned indicating zones along the rod. There is then the useful effect that only the rod projects to a greater or lesser extent out of the fluid. Owing to the constant diameter of the rod there is therefore a simple relationship between the upthrust force and the specific gravity and therefore of the concentration that is to be ascertained. The submersible member affixed to the rod nevertheless provides a high overall upthrust force and for this reason a high degree of accuracy.

As part of a specially simple and therefore particularly preferred form of the invention, the sensing means may comprise at least one stationary optical transmitter, preferably in the form of an LED, and at least one optical receiver that is spaced from and placed opposite the LED and is preferably in the form of a photoelectric cell, the marker being in the form of an optical marker and placed between the transmitter and the receiver. The use of light to sense the marker gives the useful effect of simple construction and at the same time a high degree of accuracy. The indicating zones may in this respect conveniently represent a so-called Gray code. This makes possible a very accurate but nevertheless compact arrangement.

Further convenient developments and forms of the invention will be seen from the following account of one working example thereof shown in the figures, and from the claims.

LIST OF THE VARIOUS VIEWS OF THE DRAWINGS

FIG. 1 is a view of an apparatus embodying the present invention as associated with an offset litho printing press for keeping constant the level of alcohol in the dampening fluid.

FIG. 2 is a view of the marker that is sensed without being mechanically contacted.

FIG. 3 is a plan view of a support receiving the marker and equipped with transmitters and receivers.

DETAILED ACCOUNT OF THE WORKING EXAMPLE OF THE INVENTION

As is a familiar fact, the non-printing areas of printing plates used in offset lithography are moistened with a dampening fluid, that in addition to water is more importantly formulated with alcohol and in some cases a small percentage of acid and/or alkali. It is important to keep the ratio of mixing as constant as possible. In FIG. 1 an offset litho printing press is indicated highly schematically at 1, whose plate cylinder 2 is inked by an inking unit 3 and is damped by dampening fluid from a dampening unit 4. The dampening unit 4 is designed with a pan for the dampening fluid. To maintain a steady state during operation the dampening fluid is circulated through a preparing system 5, which furthermore serves to make good the consumption of the dampening fluid. To do this the preparing system 5 has supply ducts 6 for the separate components. The duct 6 for the alcohol is connected with a tank 7 and has a valve 8 that may be opened and shut to a greater or lesser extent, that is operated in the present case by a servo motor 9 in the form of a solenoid.

The device for keeping constant the alcohol concentration or level in the dampening fluid comprises a vessel 12 placed in circuit with the preparing system 5 and in the present case is placed upstream therefrom. The vessel 12 has a bottom inlet 10 and an overflow 11 placed at a higher level than it. A float 13 is accommodated in the vessel 12 and it has a marker 14 fixed to it, whose position is sensed by a sensing device 15 that is stationary. As the reader will best be able to see from FIG. 2, the marker 14 is provided with superposed indicating zones 16, that each correspond to and denote a given concentration. The sensing device 15 is in this respect so positioned that one indicating zone 16 is sensed or detected at a time. Which of the zones is sensed is dependent on how deep the float 13 is submersed in the liquid in the vessel 12. This depth of submersion depends in turn on the specific gravity of the displaced fluid, since the upthrust acting on the float, viz., the weight of displaced fluid has to be in equilibrium with the overall weight of the float 13 and the marker 14. This is a measure of the concentration of alcohol, since the specific gravity of the dampening fluid varies with the alcohol concentration in accordance with a known relationship. The zones 16 therefore each have indicia, able to be read by the sensing means 15, concerning the respective concentration of the alcohol correlated with a given depth of immersion. The values or output signals at the output terminal of the sensing device 15 therefore represent true values for the actual alcohol level and may be used directly as input quantities or control signals for automatically controlling the alcohol concentration.

As the reader will further see from FIG. 1 as well, the float 13 is made up of a submersible (i.e. totally submersed) member 17 which never emerges from the dampening fluid in the vessel 12 and a rod 18 projecting upwards from such member 17 and passing through the surface 19 of the fluid. The marker 14 is joined to the rod 18. The diameter of the rod 18 is small in comparison with the diameter of the submersible member 17 and is uniform along the full length so that the geometrical relationships including the depth of immersion that are controlling for ascertaining the alcohol concentration are simple. The length of the rod 18 is equal to at least the overall height of the marker 14, viz., the overall height of all the ladder of indicating zones 16. The desired level of the submersible member 17 may be adjusted by weighting it or in some other way.

The height of each one individual indicating zone 16 placed in the ladder or vertical scale is in accordance with one unit of measurement of the alcohol concentration as dependent on the desired accuracy of measurement. Under working conditions it is desirable for the alcohol concentration to be kept constant to within 0.5%. The height of each indicating zone 16 is therefore equal to a change in the depth of submersion of the float 13 occuring with a change in the alcohol concentration of 0.5%. If the dependence of the depth of submersion on the alcohol concentration were to be linear, then all the indicating zones 16 would be of the same height. The said dependence or curve is however not linear. This non-linearity may be allowed for by a variation in the height of the separate indicating zones, as has been shown by way of example in FIG. 2 on the basis of the height of the indicating zones 16a and 16b respectively. The indicating zone 16a has a comparatively small height a. This means that the depth of submersion of the float 13 will change only a comparatively small amount here for a change in concentration of 0.5%. The indicating zone 16b on the other hand has a comparatively large height b. This means that the depth of submersion of the float 13 changes comparatively greatly over the (numerically equal) associated alcohol concentration range. The expedient in connection with the variation in the height of the separate indicating zones makes it possible for the alcohol concentration curve to be linearized.

The marker 14 is sensed by or read by the sensing device 15 without mechanical contact. In the illustrated working example of the invention the marker 14 is in the form of an optical marker, in the case of which the intensity of the light transmitted therethrough is a measure of the alcohol concentration. Accordingly the sensing device 15 is designed with at least one optical transmitter 20, as for example the LED, and at least one receiver 21, as for example in the form of a photoelectric cell. The indicating zones 16 are so designed that at some points they transmit light and at other points they are opaque so that the desired indicia or information may be read. In the illustrated working example of the invention the indicating zones 16, as will be seen from FIG. 2, are designed as segments of a Gray code, the code breadth being six bits. Accordingly each indicating zone 16 is subdivided into six adjacently placed zones, that are transparent and opaque in accordance with the scheme of the Gray code. In FIG. 2, for example, the shaded part is to be opaque and the other part is to be transparent.

In keeping with a code breadth of six bits the sensing device 15, see FIG. 3, is designed with six adjacent transmitters 20 and six adjacent receivers 21, that are each associated with one of the six of the sections of the indicating zones 16. These adjacently placed transmitters 20 and receivers 21 in the form of LEDs and photoelectric cells respectively are mounted on a support 22, that has a slot 23 representing the distance between the transmitters and receivers, the marker 14 to be sensed running into this slot 23. The marker 14 may for example be in the form of the card, printed with the Gray code, of transparent material mounted in a frame 24 that may slide in the slot 23. The support 22 is stationary in relation to the vessel, because for example the carrier 22, see FIG. 1, is joined to the vessel 12 that in turn is joined to a suitable stationary frame 25.

The value produced by the contactless sensing of the marker 14 by means of the sensing device 15 is regarded as an input quantity or control signal that is compared with a set point. Any deviation between the input quantity and the set point is changed into a command t to open or shut the valve 8 for the alcohol inlet duct 6. To this end, see FIG. 1, a controller 28 is present having a control signal input terminal 26 and a set point input terminal 27, the former being joined with the output of the sensing device 15 and the latter being joined with a device 29 supplying the set point. The photoelectric cells forming the receivers 21 of the sensing device 15 act as photoelectric transducers, that supply an electrical signal in accordance with the incident light. The adjustable device 29 for generating the set point can be simply in the form of a potentiometer. The transmitters 20 may be in operation all the time. The receivers 21 are interrogated by the controller 28 simultaneously or sequentially. To put into operation and control the sensing device 15 and the controller 28 there is a control unit 30 that is able to be turned on and off manually. It would be possible for the control unit 30 to be integrated in the controller 28. With the help of the values or output signals produced at the switching output 34 of the controller 28 the servo motor 9, in the present case in the form of an electromagnet, for the value 8 is so controlled that the valve 8 is kept open when the quantity of alcohol is insufficient and is kept closed when the amount of alcohol is excessive. The interrogation of the receivers 21 takes place at short intervals. To cause this to take place, the controller 28 has its output connected with an integrator 31 having a memory 32. The interrogated values are stored in the memory 32 and integrated. An average value is produced from the integrated values that is used as a signal for driving the electromagnet motor 9. Simultaneously the values are indicated by means of the digital display 33 driven by the integrator 31. It is therefore possible for the pressman to keep a continuous visible check on the alcohol level in the dampening fluid. The coding of the marker 14 and the design of the form of the sensing device 15 with one transmitter-receiver unit for each bit automatically yields a digital form of the detected values so that digital display thereof is facilitated. It would be possible for the integrator 31 and/or the display 33 driven thereby and/or the servo motor 9 also driven thereby to be integrated as parts of the controller 28.

We claim:

1. An apparatus for regulating the ratio of mixing of a component with a liquid comprising a vessel for containing a sample of said liquid, a float in said vessel, said vessel having an inlet and an overflow, a controller designed for cooperation with said float, a vertically extending marker on said float and arranged to be moved thereby in accordance with a relative level of said float in said liquid, said marker having indicating zones with indicia thereon, said zones being placed one above the other and vertically aligned on said marker in the length direction thereof, said zones having different respective vertical heights corresponding to units of concentration of said component in said liquid in accordance with a non-linear relationship between amounts of said component added to said liquid and resulting changes in the specific gravity thereof, a sensing device adapted to be responsive to said zones at different levels of said float relative to said liquid, said sensing device being designed to produce control signals representative of said zones in accordance with said level of said float in said liquid sample, said controller having a control signal input connection for such control signals, a set point input connection and at least one servo signal output for controlling the composition of said liquid.

2. The apparatus as claimed in claim 1 wherein said float comprises a submersible member and a rod attached thereto to connect it with said marker, said rod having a constant cross section and a length that is at least equal to the height occupied by said zones placed vertically one above the other.

3. The apparatus as claimed in claim 1 wherein said sensing device comprises at least one stationarily mounted optical transmitter and at least one optical receiver placed opposite to and spaced from said transmitter, said marker being in the form of a optical indicating means placed between said transmitter and said receiver.

4. The apparatus as claimed in claim 3 wherein said transmitter and said receiver respectively comprise an LED and a photoelectric cell.

5. The apparatus as claimed in claim 3 comprising a support fixed to said vessel and having a slot with the transmitter and receiver placed on opposite sides thereof, said marker being movable in said slot.

6. The apparatus as claimed in claim 1 wherein said marker is encoded with each of said zones forming one segment of such code and having six bits, said receiver and said transmitter each comprising six LEDs and six photoelectric transducers respectively.

7. The apparatus as claimed in claim 3 wherein said controller is adapted to interrogate said receiver.

8. The apparatus as claimed in claim 1 comprising a servo motor adapted to be driven by said controller and a valve adapted to be operated by said servo motor for the control of the rate of supply of said component into said liquid into a liquid circuit.

9. The apparatus as claimed in claim 8 comprising a memory and an integrator connected between said controller and said servo motor.

10. The apparatus as claimed in claim 1 comprising a digital display adapted to be driven by said controller.

11. The apparatus as claimed in claim 1 wherein the liquid is a dampening liquid of an offset lithopress and the component is alcohol, comprising means adapted to control the supply of alcohol into the dampening liquid.

* * * * *